(12) United States Patent
Erhardt

(10) Patent No.: US 7,164,027 B2
(45) Date of Patent: Jan. 16, 2007

(54) ARALKYL ESTER SOFT DRUGS

(75) Inventor: Paul W. Erhardt, Sylvania, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 10/857,683

(22) Filed: May 28, 2004

(65) Prior Publication Data
US 2004/0224924 A1   Nov. 11, 2004

Related U.S. Application Data

(62) Division of application No. 09/570,485, filed on May 12, 2000, now Pat. No. 6,750,238.

(51) Int. Cl.
C07D 233/78    (2006.01)
(52) U.S. Cl. .................................................. 548/321.1
(58) Field of Classification Search .............. 548/321.1
See application file for complete search history.

(56) References Cited

U.S. PATENT DOCUMENTS

| | | | |
|---|---|---|---|
| 3,150,137 A | 9/1964 | Buzas | |
| 3,636,010 A | 1/1972 | Anner et al. | |
| 4,093,721 A | 6/1978 | Phillipps et al. | |
| 4,163,058 A * | 7/1979 | Stella et al. ................ | 514/391 |
| 4,304,781 A | 12/1981 | Crossley | |
| 4,387,103 A | 6/1983 | Erhardt et al. | |
| 4,405,642 A | 9/1983 | Kam et al. | |
| 4,450,173 A | 5/1984 | Erhardt et al. | |
| 4,505,926 A | 3/1985 | Newsome et al. | |
| 4,508,725 A | 4/1985 | Matier et al. | |
| 4,556,668 A | 12/1985 | Erhardt et al. | |
| 4,593,119 A | 6/1986 | Erhardt et al. | |
| 4,604,481 A | 8/1986 | Kam et al. | |
| 4,623,652 A | 11/1986 | Erhardt et al. | |
| 4,692,446 A | 9/1987 | Erhardt et al. | |
| 4,804,677 A | 2/1989 | Erhardt et al. | |
| 4,906,661 A | 3/1990 | Erhardt et al. | |
| 4,929,623 A | 5/1990 | Abe et al. | |
| 5,849,788 A | 12/1998 | Druzgala | |
| 6,114,344 A | 9/2000 | Druzgala et al. | |
| 6,130,240 A | 10/2000 | Druzgala | |
| 6,159,665 A | 12/2000 | Chin et al. | |
| 6,316,487 B1 | 11/2001 | Druzgala et al. | |
| 6,362,223 B1 | 3/2002 | Druzgala et al. | |
| 6,372,783 B1 | 4/2002 | Druzgala et al. | |
| 6,387,914 B1 | 5/2002 | Druzgala et al. | |
| 6,469,064 B1 | 10/2002 | Druzgala | |
| 2001/0056119 A1 | 12/2001 | Druzgala et al. | |
| 2002/0013330 A1 | 1/2002 | Druzgala et al. | |
| 2002/0025970 A1 | 2/2002 | Druzgala et al. | |
| 2002/0045620 A1 | 4/2002 | Druzgala et al. | |
| 2002/0143002 A1 | 10/2002 | Hochberg | |
| 2002/0169208 A1 | 11/2002 | Druzgala | |
| 2002/0183343 A1 | 12/2002 | Druzgala | |
| 2002/0193428 A1 | 12/2002 | Druzgala et al. | |

FOREIGN PATENT DOCUMENTS

| | | |
|---|---|---|
| EP | 0 640 601 B1 | 3/1995 |
| EP | 0 703 910 B1 | 4/1996 |
| WO | WO 02/40052 A2 | 5/2002 |
| WO | WO 02/096855 A2 | 12/2002 |

OTHER PUBLICATIONS

Fetter et al., Acta Chimica Academiae Scientiarum Hungaricae (1973), 78(3), pp. 325-333.*
N. Bodor and P Buchwald; Drug Targeting via Retrometabolic Approaches; Pharmacol. Ther. vol. 76, Nos. 1-3, pp. 1-27, (1997).
R. Albrecht and O. Loge; B2-Agonists containing metabolically labile groups II. The influence of ester groups in the aryl system. Eur. J. Med.Chem-Chim Ther. 20. N 1, pp. 57-60 (1989).
A. Juhasz and N. Bodor; Cardiovascular studies on different classes of soft drugs; Parmazie 55:228-238 (2000).
M.J. Pekka Raatikainen, C.A. Napolitano, P. Druzgala and D.M. Dennis; Electrophysiological Effects of a Novel, Short-Acting and Potent Ester Derivative of Amiodarone, ATI-2001, in Guinea Pig Isolated Heart; The Journal of Pharmacology and Experimental Therapeutics; vol. 227, No. 3, pp. 1454-1463 (1996).
T.E. Morey, C.N. Seubert, M.J. Pekka Raatikainen, A.E. Martynyuk; P. Druzgala, P. Milner, M.D. Gonzalez and D.M. Dennis; Structure-Activity Relationships and Electrophysiological Effects of Short-Acting Amiodarone Homologs in Guinea Pig Isolated Heart; The Journal of Pharmacology and Experimental Therapeutics; vol. 297, No. 1, pp. 260-266 (2001).

(Continued)

Primary Examiner—Laura L. Stockton
(74) Attorney, Agent, or Firm—MacMillan, Sobanski & Todd, LLC

(57) ABSTRACT

The present invention describes a method for programming a specific course and rate of metabolism for a parent drug compound that leads to an inactive or very weakly active and nontoxic metabolite when the modified drug compound is administered. The parent drug compound is modified by forming one or more of a predetermined chemical arrangement within the parent drug structure where the chemical arrangement is A-Ø-(R)—X—R'; where A is absent or is a tether moiety which allows for a metabolically stable chemical connection to be made to the parent drug compound; Ø is a substituted aryl or heteroaryl system that is already present within the parent drug compound or is specifically added to the parent drug compound via A; R is an alkyl or alkene containing chain either branched or unbranched from 0 to 10 carbons that is either also already present within the parent drug compound or is specifically added to the parent drug compound via connection to Ø; X is a carboxyl, sulfoxyl or phosphatyl function that is specifically added to the parent drug compound via connection to R; and, R' is an added alkyl, alkenyl, or aralkyl group either branched or unbranched containing from 1 to 10 carbons, other common leaving group, or a structural element already present as an inherent portion of the parent drug compound.

2 Claims, 10 Drawing Sheets

OTHER PUBLICATIONS

M.J. Pekka Raatikainen, T.E. Morey, P. Druzgala, P. Milner, M.D. Gonzalez, and D.M. Dennis; Potent and Reversible Effects of ATI-2001 on Atrial and Atrioventricular Nodal Electrophysiological Properties in Guinea Pig Isolated Perfused Heart; The Journal of Pharmacology and Experimental Therapeutics; vol. 295, No. 2, pp. 779-785 (2000).

R. Albrecht and O. Loge; $B_2$—Agonists containing metabolically labile groups. I. The influence of ester groups in the nitrogen substituent; Eur. J. Med. Chem.-Chim. Ther. 20., No., pp. 51-55 (1985).

O. Rosen and F. Sandberg; Studies on N-Substituted Barbituric Acid Derivatives. II; Acta Chemica Scandinavica 675-687 (1950).

H.-S. Yang, W.-M. Wu and N. Bodor, Soft Drugs. XX. Design, Synthesis, and Evaluation of Ultra-Short Acting beta-Blockers, *Pharm. Res.*, 12, 329-336 (1995).

M. Graffner-Nordberg, K. Sjodin, A. Tunek and A. Halberg, Synthesis and Enzymatic Hydrolysis of Esters, Constituting Simple Models of Soft Drugs, *Chem.Pharm.Bull.*, 46, 591-601 (1998).

R.M. Long and R.M. Weishilbourn, Recommendations of the NIGMS Working Group-Understanding Individual Variations in Drug Responses: From Phenotype to Genotype, *NIH Report* http://www.hih.gov/nigms/news/reports/pharmaceogentics.html, 5 pages (Jun. 9-10, 1998).

P.W. Erhard, Benzylamine and Dibenzylamine Rvisited. Syntheses of N-Substituted Aryloxypropanolamines Exemplifying a General Route to Secondary Aliphatic Amines, *Synth. Comm.*, 13, 103-113 (1983).

P.W. Erhardt, C.M. Woo, W.G. Anderson and R.J. Gorcynski, Ultra Short-Acting β-Adrenergic Receptor Blocking Agents. 2. (Aryloxy)propanolamines Containing Esters in the Aryl Function, *J.Med.Chem.*, 25, 1408-1412 (1982).

P.W. Erhardt, C.M. Woo, W.L. Matier, R.J. Gorcynski and W.G. Anderson, Ultra-Short-Acting β-Adrenergic Receptor Blocking Agents. 3. Ethylenediamine Derivatives of (Aryloxy)propanolamines Having Esters on the Aryl Function, *J.Med.Chem.*, 26, 1109-1112 (1983).

P.W. Erhardt, *Esmolol.* In *Chronicles of Drug Discovery*, D. Lednicer, Ed. ACS Books, Washington D.C., U.S.A. 191-206 (1993).

P.W. Erhardt, A Prodrug and a Soft Drug. P.W. Erhardt, in *Drug Metabolism: Databases and High-Throughput Testing During Drug Design and Development*, Ed. IUPAC Books, Blackwell Science, Oxford, U.K., 62-69 (1999).

D.M. Stout, L.A. Black, C.L. Barcelon-Yang, W.L. Matier, B.S. Brown, C.Y. Quon and H.F. Stampfli, Ester Derivatives of 2,6-Bis (1-pyrrolidinylmethyl)-4-benzamidophenol as Short-Acting Antiarrhythmic Agents. 1., *J.Med.Chem.*, 32, 1910-1913 (1989).

R.J. Chorvat, L.A. Black, V.V. Ranade, C. Barcelon-Yang, D.M. Stout, B.S. Brown, H.F. Stampfli and C.Y. Quon Mono and Bis(aminomethyl)phenylacetic Acid Esters as Short-Acting Antiarrhythmic Agents. 2., *J.Med.Chem.*, 36, 2494-2498 (1993).

P.W. Erhardt, Drug Metabolism Data: Past, Present, and Future Considerations, *Med.Chem.Res.*, 8, 400-421 (1998).

P.W. Erhardt, Drub Metabolism Data: Past Present and Future Considerations, *Metabolism Databases and High Through-put Testing During Drug Design and Development*, Ed. IUPAC Books, Blackwell Science, Oxford, U.K. 2-15 (1999).

P.W. Erhardt, Statistics-Based Probabilities of Metabolic Possibilities, *Metabolism Databases and High Through-put Testing During Drug Design and Development*, Ed. IUPAC Books, Blackwell Science, Oxford, U.K., 185-191 (1990).

P.W. Erhardt, Comparison of Commercially Available Metabolism Databases During The Design of Prodrugs and Codrugs, *Metabolism Databases and High Through-put Testing During Drug Design and Development*, Ed. IUPAC Books, Blackwell Science, Oxford, U.K., 208-222 (1999).

P. Buchwald and N. Bodor, Quantitative Structure-Metabolism Relationships: Steric and Nonsteric Effects in the Enzymatic Hydrolysis of Noncongener Carboxylic Esters, *J.Med.Chem.*, 42, 5160-5167 (1999).

N.C. Dhar, R.B. Maehr, L.A. Masterson, J.M. Midgley, J.B. Stenlake and W.B. Wastila, Approaches to Short-Acting Neuromuscular Blocking Agents: Nonsymmetrical Bistertrahydroisoquinolinium Mono-and Diesters, *J.Med.Chem.*, 39, 556-561 (1996).

W.O. Foye, T.L. Lemke, D.A. Williams, Principles of Medicinal Chemistry, Eds., Williams & Wilkins Publ., Baltimore, MD, p. 356 (1995).

N. Bodor, P. Buchwald, Soft Drugs Designs: General Principals and Recent Applications, *Med.Res.Rev.*, 20, 58-101 (2000).

D.A. Matthews, et al., Dihydrofolate Reductase: X-ray Structure of the Binary Complex with Methotrexate, Science, 197, 452-455 (1977).

*The Physicians Desk Reference* (PDR) 50th ed., Publ:Med. Econ. Co., Montvale, NJ, p. 1275-1279 (1996).

N. Bodor, Designing Safer Ophthalmic Drugs by Soft Drug Approaches, *Journal of Ocular Pharmacology*, vol. 10, No. 1, p. 3-15 (1994).

N. Bodor, P. Buchwald, and M.-J. Huang, The Role of Computational Techniques in Retrometabolic Drug Design Strategies, Computational Molecular Biology Theoretical Computational Chemistry, vol. 8, Chapter 15, 569-618. (1999).

N. Bodor, P. Buchwald and M.-J.Huang, Computer Assisted Design of New Drugs Based on Retrometabolic Concepts, SAR and QSAR in Environmental Research, vol. 8, pp. 41-92, (1998).

Search Report From International Application PCT/USO01/15146 which corresponds to this U.S. application, Sep. 19, 2001.

Liao, Jing, Thesis for Master of Science Degree in Medicinal Chemistry entitled *Development of Soft Drugs For the National Population*, The University of Toledo (Dec. 2000) (147 pages).

Tagat et al., "Synthetic Inhibitors of Interleukin-6 1: 2,3,7,8-Tetrahydro-4-Aryl-1H-Cyclopent[e]imidazo [1,2-a]-Pyridin-5(6H)-One and Related Compounds." Bioorganic & Medicinal Chemistry Letters, vol. 5(18), pp. 2139-2142, 1995.

P.W. Erhardt, "Medicinal Chemistry in the New Millenium, A Glance into the Future." Pure Appl. Chem. vol. 74, No. 5, pp. 703-785 (2002).

Search Report from PCT/US03/36700 dated May 27, 2004 (PHR00502).

Search Report from PCT/US03/36686 dated Jun. 17, 2004 (PHR00402).

* cited by examiner

10 Y = NH
11 Y = O

ARALKYL ESTER SOFT DRUGS

CROSS-REFERENCE TO RELATED APPLICATION

The present invention is a divisional application of U.S. Ser. No. 09/570,485 filed May 12, 2000, now U.S. Pat. No. 6,750,238 now allowed, which is expressly incorporated herein by reference.

BACKGROUND AND SIGNIFICANCE OF THE INVENTION

Pharmaceutical agents or drugs exhibit desirable therapeutic properties because they contain distinct molecular arrangements called pharmacophores. Oftentimes, however, the pharmacophores or the presence of other chemical components within such compounds, provide a less than ideal overall profile relative to the final deployment of a given drug for a particular clinical indication. In some cases this situation can be improved by altering chemical features associated with a drug's distribution, metabolism or elimination (DME). This process, when successful, results in what is now referred to in the pharmaceutical community as a "soft drug" version of the original or parent drug compound: *Soft Drugs. XX. Design, Synthesis and Evaluation of Ultra-ShortActing beta-Blockers*, H.-S. Yang, W.-M. Wu and N. Bodor, Pharm. Res., 12, 329 (1995); and *Synthesis and Enzymatic Hydrolysis of Esters, Constituting Simple Models of Soft Drugs*, M. Graffner-Nordberg, K. Sjodin, A. Tunek and A. Hallberg, Chem. Pharm. Bull., 46, 591 (1998).

However, unless there is compelling preclinical data which suggests that the clinical application of a lead compound is going to become problematic, DME-related features are typically not rigorously evaluated in a chemical manner during the early process of new drug discovery and development. This situation has arisen, in part, because substantial clinical experience is often required to accurately define the sometimes subtle parameters of an undesirable DME feature relative to the beneficial aspects of a new drug while the latter is within the close purview of its actual clinical use in a specific pathophysiological setting. The problem of not knowing exactly what DME and toxicity-related properties may need to be addressed is additionally confounded by not having ready chemical blueprints for how to generally proceed even when a particular DME or toxicity issue becomes suspected.

The invention disclosed herein provides a ready method for altering DME and toxicity-related properties by deploying a specific chemical blueprint. The approach is useful to initially assess the DME parameters for an entire family of potential new drug candidate possibilities during the family's very early stages of structural refinement and preclinical study. When applied in this fashion, the inventive method expedites and improves the efficiency of the overall process of drug discovery and development.

Technologies which can enhance the efficiency of the drug discovery and development process have recently become of very high interest to the global pharmaceutical enterprise: *Lead Generation and Optimization*, Annual Meeting Strategic Research Institute, San Diego, Jun. 23, 1997; *Emerging Technologies for Drug Discovery*, International Biotechnology Event National Management Health Care Congress, Boston, May 19, 1997; and *Pharmaceutical Education*, Interim Meeting, American Association Colleges Pharmacy, Washington, D.C., Mar. 2, 1997.

Of equal significance but in more succinct and individually directed applications, the present invention is also useful for modifying the clinically established pharmaceutical agents where the specific therapeutic/side-effect details and benefits that might be associated with such DME alterations to a parent drug molecule are already recognized for a given indication. The current move to individualize drug treatment protocols within the evolving field of pharmacogenetics further underscores the very high interest and importance for having conveniently deployable technologies which can be generally applied toward fine-tuning and tailoring the overall pharmacological profile of a given drug for a given indication within a given individual: *Recommendations of the NIGMS Working Group-Understanding Individual Variations in Drug Responses: From Phenotype to Genotype*, R. M. Long and R. M. Weinshilboum, NIH Report 5 pages (Jun. 9–10, 1998).

SUMMARY OF THE INVENTION

The present invention relates to a method of deploying one or more aralkyl ester moieties or "metabophores" within a parent drug compound. The aralkyl ester moieties are either co-constructed within the constitutive molecular framework of a parent drug compound or are added onto a parent drug compound as a distinct appendage. In all instances these constructions are done in such a manner so as to preserve the parent drug's therapeutical properties while programming a specific course for the drug's metabolism. The specific course for the drug's metabolism leads to inactive or much less active, non-toxic metabolites when the modified drug is then administered to humans by either the oral, inhalation, injection, implantable or topical routes.

Furthermore, the specific molecular details of the aralkyl ester moieties and their various placements within the parent drug's structure are able to be fine-tuned to precisely control the rate of metabolism. The rate of metabolism, in turn, can be used to control the distribution, the duration of action, the elimination, and/or the toxicity of the resulting soft drug.

The present invention is useful for all drug types whenever the programmed ester cleavage causes fragmentation of the drug's inherent pharmacophore or leads to the production of an acidic group that can not somewhere by tolerated by the pharmacophore within the still intact parent drug.

The present invention is useful for producing families of closely related compounds for better optimizing the overall pharmacological profiles of new drug candidates during the process of drug design and development.

The present invention is also useful for enhancement of the overall therapeutic profiles for a wide variety of drugs already being used.

In one aspect of the present invention, the metabophores are used to program a specific course of innocuous metabolism/elimination in order to circumvent unwanted accumulation and/or toxic pathways otherwise exhibited by the parent drug.

In another aspect, the present invention is used to program the rate for a specified metabolism in order to adjust the parent drug's duration of action to a desired shorter time interval. Alternatively, when the aralkyl ester moieties of the present invention are used in conjunction with an implant or drug depot delivery system, the rate of programmed metabolism can be matched to that for the soft drug's delivery so as to precisely provide prolonged steady-state levels of the soft drug at pre-calibrated concentrations.

In another aspect, the present invention is used to program an ultra-short duration into a parent drug to allow the resulting soft drug's actions to be under precise moment-to-moment control via its intravenous administration infusion rate, an overall drug property which has already been demonstrated to be particularly useful in critical care and surgical settings. Given the paucity of drugs and drug-related technologies that have been previously targeted for very young humans, the present invention is especially useful in the development of aralkyl ester soft drugs which are conveniently and safely deployed for the specific treatment of premature, full-term newborn or for the perinatal and neonatal populations in general.

In yet another aspect of the present invention, the metabophore is useful to provide an ultra-short duration drug which allows for localizing the effects of the soft drug when the drug's initial delivery or activation within a desired compartment can also be achieved in a selective manner (e.g. localized injection, implant, surgical sutures, or localized photodynamic activation).

In still yet another aspect of the present invention, the metabophores are useful to provide a soft drug pharmacological agent that can be deployed by the intravenous route to wean a patient off of a parent drug whose pharmacological action is more safely removed in a controlled, step-wise manner by progressively decreasing the rate of the intravenous drip of the soft drug version (e.g. avoidance of rebound pharmacological events due to abrupt withdrawal of the parent compound).

Finally, the present invention is useful with drugs which are administered topically to the skin, eye or nasal passageways in order to eliminate or lessen any unwanted effects that the parent drugs might otherwise exhibit upon their absorption into the systemic circulation.

DESCRIPTION OF THE INVENTION

Figure 1:
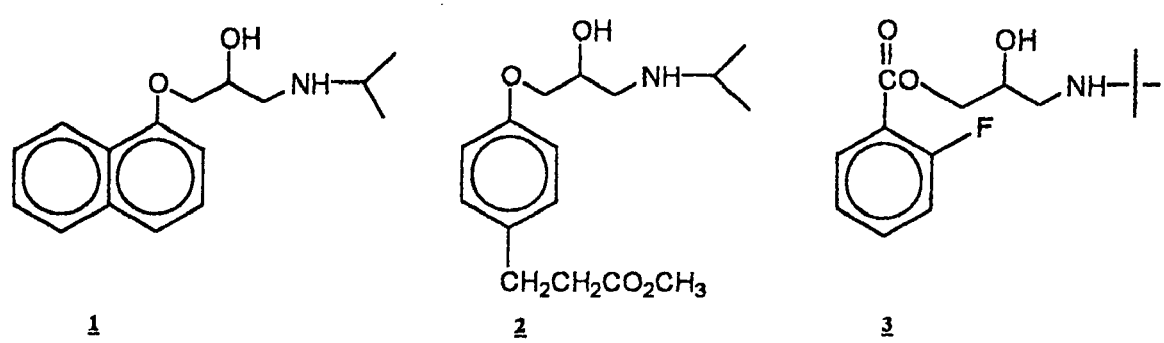
FIG. 1 shows Structure 1 which is propranolol, a prototypical aryloxypropanolamine beta-adrenergic receptor blocking agent which is used clinically and has a long duration of action (i.e. several hour half-life). Structure 2 is esmolol, which is also a beta-blocker used clinically (Brevibloc®) but was designed to have an ultra-short duration of action (i.e. ten minute half-life) as a result of an appended "external" ester (note carboxyl moiety extended from the southern region of the overall molecule). Structure 3 is another ultra-short acting beta-blocker which has an ester within or "internal" to the parent aryloxypropanolamine pharmacophore (note centralized location of the carboxyl moiety within the overall molecule).

The present invention relates to a method for programming a specific course and rate for a parent drug compound's metabolism that leads to an inactive or very weakly active and non-toxic metabolite when the parent drug compound is administered to humans by either the oral, injection, inhalation, implatable or topical routes. The method comprises modifying the parent drug compound by forming one or more of a modifying the parent drug compound by forming one or more of a predetermined chemical arrangement within the parent drug compound. The chemical arrangement comprises A-Ø-(R)—X—R' where A is absent or is a tether moiety which allows for a metabolically stable chemical connection to be made to the parent drug compound. Ø is a substituted aryl or heteroaryl system that is already present within the parent drug compound or is specifically added to the parent drug compound via A. R is an alkyl or alkene containing chain either branched or unbranched from 0 to 10 carbons that is either already present within the parent drug compound or is specifically added to the parent drug compound via connection to Ø. X is a carboxyl, sulfoxyl or phosphatyl function that is specifically added to the parent drug compound via connection to R. R' is an added alkyl, alkenyl, or aralkyl group either branched or unbranched containing from 1 to 10 carbons; other common leaving group; or, a structural element already present as an inherent portion of the parent drug compound. The chemical arrangement is not used in connection with specific structural settings where the parent drug compound is an aryloxypropanolamine, a 2,6-bis(1-pyrrolidinylmethyl)-4-benzamidophenol, or where the parent drug already contains an ester moiety as an inherent component of its structure that also causes the parent drug to already exhibit a short duration of action as would be the specific cases for the classical short-acting drugs succinylcholine and procaine.

In a preferred method only one chemical arrangement is used. In certain preferred embodiments, X is carboxyl. In other embodiments, R and R' are unbranched alkyl from 1 to 2 carbons. In still other embodiments, R' is a structural element already present as an inherent portion of the parent drug.

The modified drug is used to optimize the overall pharmacological profile of a new drug candidate during the process of drug design and development. Alternatively, the modified drug is used to enhance the overall therapeutic profile of a parent drug already being used in the clinic. The programmed metabolism of the added chemical arrangement serves to circumvent unwanted accumulation of the drug and to circumvent one or more toxic metabolic pathways.

The programmed rate of metabolism for the added chemical arrangement is adjusted to produce a shorter duration of action for the modified drug as compared to the parent drug. The shorter duration allows the actions of the modified drug to be under precise moment-to-moment control by adjustment of the infusion rate of the modified drug when administered intravenously. The intravenous administration is used to treat critical care patients and to treat neonates.

The intravenous administration is also used to wean a patient off an unmodified parent drug whose similar pharmacological action is more safely removed in a controlled, step-wise manner by progressively decreasing the rate of the intravenous drip of the modified drug. The shorter duration allows the actions of the modified drug to remain localized when the initial delivery or activation of the modified drug is targeted to a specified compartment by use of localized injection or implant materials, or by localized photodynamic activation of the modified drug. In certain embodiments, the implant is a type of surgical-related material or suture where the modified drug is an antibiotic or a compound that promotes healing.

According to the present invention, the programmed rate of metabolism of the modified drug is matched with a, release rate from a sustained-release injectable formulation or implant of the modified drug to provide for prolonged steady-state levels of the modified drug at pre-calibrated concentrations.

Also, according to the present invention, the modified drug is used as a topical treatment in order to eliminate or lessen unwanted effects that the unmodified parent drug exhibits upon systemic absorption after placement on the skin or within the eye or nasal passageways.

The method of the present invention is especially useful where the parent drug plus added chemical arrangement comprises a short-acting anti-cholinergic agent. In certain embodiments, the short-acting anti-cholinergic agent is an atropine derivative that is designed for topical administration to the eye. In other embodiments, the short-acting anti-cholinergic agent is a non-depolarizing neuromuscular junction blocking agent that is designed for use by the intravenous route during surgical-related procedures.

Also, the method the present invention is especially useful where the parent drug plus added chemical arrangement comprises an ultra-short acting $alpha_1$-adrenergic receptor blocker or an $alpha_2$-adrenergic receptor agonist.

The method of the present invention is also useful where the parent drug plus added chemical arrangement comprises a short-acting inhibitor of the sodium channel. In certain embodiments, the short-acting inhibitors are administered as sustained-release or implantable dosage forms.

Still other uses of the method of the present invention include uses in which the parent drug plus the added chemical arrangement comprises an ultra-short acting ACE inhibitor; an ultra-short acting histamine receptor blocker; an ultra-short acting adenosine antagonist; an ultra-short acting anti-inflammatory agent; an ultra-short acting antiarrhythmic agent; and, an ultra-short acting calcium channel blocker.

Still further uses of the method of the present invention include uses in which the parent drug plus the added chemical arrangement comprises an ultra-short acting antibiotic compound including sulfonamide, penicillin, cephalosporin or tetracycline. In certain embodiments, the ultra-short acting antibiotic compounds are administered via their impregnation in surgical suture material or wound-healing implantable polymeric materials.

Yet another use of the method of the present invention includes a use in which the parent drug plus the added chemical arrangement comprises a short-acting version of methotrexate. In certain embodiments, the short-acting version of methotrexate is administered topically. The present invention is especially useful where the topical administration is used to treat epidermoid cancers or psoriasis.

Referring now to Structures 2 and 3 in FIG. 1, the indicated metabophoric functionalities were previously incorporated into propanol-like structures to produce ultra-short acting beta-adrenergic receptor blocking agent soft drugs: Method for Treatment or Prophylaxis of tetra-substituted Cardiac Disorders (Aryl Esters), P. W. Erhardt, R. J. Borgman and J. P. O'Donnell, U.S. Pat. No. 4,387,103 (1983); Method for Treatment or Prophylaxis of Cardiac Disorders (Aryl Esters), P. W. Erhardt, R. J. Borgman and J. P. O'Donnell, U.S. Pat. No. 4,593,119 (1986); Method for Treatment or Prophylaxis of Cardiac Disorders (Internal Esters), S. T, Kam, P. W. Erhardt, R. J. Borgman and J. P. O'Donnell, U.S. Pat. No. 4,405,642 (1983); Compounds and Method for Treatment or Prophylaxis of Cardiac Disorders (N-External Esters), P. W. Erhardt and R. J. Borgman, U.S. Pat. No. 4,450,173 (1984); Compounds for Treatment or Prophylaxis of Cardiac Disorders (Internal Esters), R. J. Borgman, P. W. Erhardt, S. T. Kam and J. P. O'Donnell, U.S. Pat. No. 4,604,481 (1986); Esters of Thiadiazole Oxypropanolamine Derivatives and Pharmaceutical Uses, P. W. Erhardt and W. L. Matier, U.S. Pat. No. 4,623,652 (1986); Esters of 3-(3-substituted-Amino-2-Hyroxypropoxy)-4-Substituted-1,2,5-Thiadiazole Derivatives, W. L. Matier, P. W. Erhardt and G. Patil, U.S. Pat. No. 4,508,725 (1985); Ethylenediamine Derivatives of Aryloxypropanolamine Aryl Esters Having Various Medicinal Properties, P. W. Erhardt and C. M. Woo, U.S. Pat. No. 4,556,668 (1985); Esters or Aryloxypropanolamine Derivatives and Medicinal Uses, P. W. Erhardt and W. L. Matier, U.S. Pat. No. 4,692,446 (1987); Esters of Aryloxypropanolamine Derivatives, P. W. Erhardt and W. L. Matier, U.S. Pat. No. 4,804,677 (1989); Esters of Aryloxypropanolamine Derivatives, P. W. Erhardt and W. L. Matier, U.S. Pat. No. 4,906,661 (1990); *Ultra-Short Acting β-Blockers: A Proposal For The Treatment Of The Critically Ill Patient*, J. Zaroslinski, R. J.

Borgman, J. P. O'Donnell, W. G. Anderson, P. W. Erhardt, S. T. Kam, R. D. Reynolds, R. J. Lee and R. J. Gorczynski, *Life Sciences*, 31, 899 (1982); *Benzylamine and Dibenzylamine Revisited. Syntheses of N-Substituted Aryloxypropanolamines Exemplifying a General Route to Secondary Aliphatic Amines*, P. W. Erhardt, *Synth. Comm.*, 13, 103 (1983); *Ultra Short-Acting β-Adrenergic Receptor Blocking Agents. 1. (Aryloxy)propanolamines Containing Esters in the Nitrogen Substituent*, P. W. Erhardt, C. M. Woo, R. J. Gorczynski and W. G. Anderson, *J. Med. Chem.*, 25, 1402 (1982); *Ultra-Short-Acting β-Adrenergic Receptor Blocking Agents. 2. (Aryloxy)propanolamines Containing Esters on the Aryl Function*, P. W. Erhardt, C. M. Woo, W. G. Anderson and R. J. Gorczynski, *J. Med. Chem.*, 25, 1408 (1982); and *Ultra-Short-Acting β-Adrenergic Receptor Blocking Agents. 3. Ethylenediamine Derivatives of (Aryloxy)propanolamines Having Esters on the Aryl Function*, P. W. Erhardt, C. M. Woo, W. L. Matier, R. J. Gorczynski and W. G: Anderson, *J. Med. Chem.*, 26, 1109 (1983). The successful development and marketing of Structure 2 (esmolol or Brevibloc®) provides an exemplary clinical proof of utility for the present invention within the context of using beta-blockers in the critical care arena: Esmolol. P. W. Erhardt, in *Chronicles of Drug Discovery*, D. Lednicer, Ed. ACS Books, Washington, D.C., U.S.A. 1993; *A Prodrug and a Soft Drug*. P. W. Erhardt, in *Drug Metabolism: Databases and High-Throughput Testing During Drug Design and Development*, P. W. Erhardt, Ed. IUPAC Books, Blackwell Science, Oxford, U.K. 1999.

Figure 2:
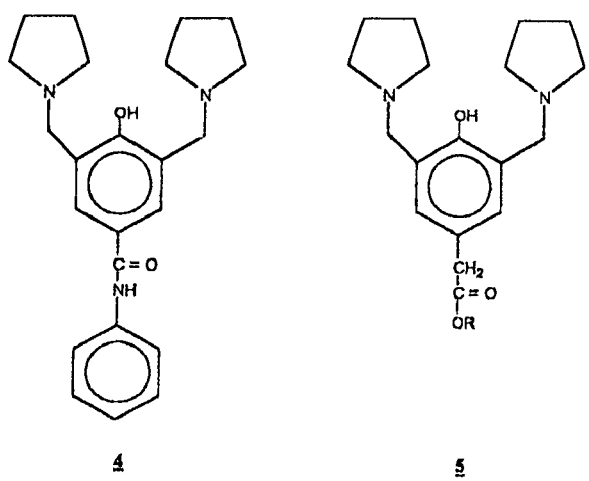
FIG. 2 shows Structure 4 which is 2,6-bis(1-pyrrolidinylmethyl)-4-benzamidophenol, an antiarrhythmic drug candidate. Structure 5 represents a series of external ester-containing derivatives of 4 that provides a complimentary family of potential soft drug versions of the parent having variously shortened durations of action.

Referring to FIG. 2, the indicated metabophoric functionalities have also been previously incorporated into a novel compound, Structure 4 as the latter was undergoing preclinical and early clinical development for its potential use as a long-acting antiarrhythmic agent. A short-acting, potential soft drug version, Structure 5, was obtained in a complimentary manner within a very limited family of closely-related compounds: *Ester Derivatives of 2,6-Bis(7-pyrrolidinylmethyl)-4-benzamidophenolas Short-Acting Antiarrhythmic Agents. 1.* D. M. Stout, L. A. Black, C. Barcelon-Yang, W. L. Matier, B. S. Brown, C. Y. Quon and H. F. Stampfli, *J. Med. Chem.*, 32, 1910 (1989); and *Mono- and Bis(aminomethyl)phenylacetic Acid Esters as Short-Acting Antiarrhythmic Agents.* 2. R. J. Chorvat, L. A. Black, V. V. Ranade, C. Barcelon-Yang, D. M. Stout, B. S. Brown, H. F. Stampfli and C. Y. Quon, *J. Med. Chem.*, 36, 2494 (1993). Although these research compounds were not pursued into the marketplace, the ready obtainment of a family of short-acting agents within the specific context of parent compound Structure 4 provides a demonstration of the utility and ease of deploying the metabophoric technology, as specifically described herein, in a parallel manner during the preclinical and early clinical development stages of new drug development.

Figure 3:
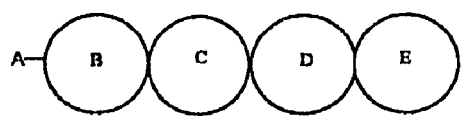
FIG. 3 shows a schematic representation of the chemical elements showing a "metabophoric" blueprint for placement within clinically used drug molecules and/or for elaboration within new drug candidate compounds undergoing development for use within the clinic. In Structure 6: A is an attachment or tether functionality when B is not an inherent portion of the parent drug molecule; B is an aryl or heteroaryl system; C is alkyl or an alkene chain; D is carboxyl ($-CO_2-$), sulfoxyl ($-SO_3-$) or a phosphatyl function ($-PO_3<$); and E is alkyl, aralkyl or an additionally derivatized leaving group. In certain embodiments, A may be deleted because B or both B and C are already present as an inherent portion of the parent structure. For example, when A is absent, B is substituted phenyl, C is ethyl, D is carboxyl and E is methyl, then Structure 6 defines the southern portion of Structure 2 plus its relationship to the phenyl ring in the right-half portion of the naphthalene system within Structure 1 wherein the latter is an inherent portion of the prototypical β-blocker pharmacophore. In Structure 7: E may also be (or become attached to) a required pharmacophoric component of the parent drug compound. In this embodiment, the ester metabophore D is thus encompassed from both sides within the parent structure's pharmacophore (e.g. as in Structure 3 within FIG. 1) as opposed to is residence as an appendage (e.g. as in Structure 2 within FIG. 1). Thus, when A is absent, B is ortho-flurophenyl, C is absent (alkyl case $-(CH_2)_n-$ where n=0), D is carboxyl and E is a methylene attached to a portion of the parent pharmacophore, then Structure 7 defines the key metabophoric placement within Structure 3 of FIG. 1.

Referring to FIG. 3, the structural arrangements specified by Structures 6 and 7 have similar applicability when placed within other drug molecules. Since the structural systems or chemical arrangements portrayed by Structures 6 and 7 program distinct metabolic lability into a parent molecule, they are also referred to herein as "metabophores," by analogy to the term "pharmacophore". The latter term is used to specify the structural components within a drug that are requisite for the drug's efficacious pharmacological activity. By analogy, the term "metabophore" has recently been placed within the literature to designate the specific molecular features that are pertinent for a given metabolic process, such as that for the enzymatic hydrolysis reaction of an ester moiety: *Drug Metabolism Data: Past And Present Status*, P. W. Erhardt, *Med. Chem. Res.*, 8, 400 (1998); *Drug Metabolism Data: Past, Present and Future Considerations*, P. W. Erhardt, *Metabolism Databases and High Through-put Testing During Drug Design and Development*, P. Erhardt, Ed. IUPAC Books, Blackwell Science, Oxford, U.K., 1999; *Statistics-Based Probabilities of Metabolic Possibilities*, P. W. Erhardt, *Metabolism Databases and High Through-put Testing During Drug Design and Development*, P. Erhardt, Ed. IUPAC Books, Blackwell Science, Oxford, U.K., 1999; and *Use of Metabolism Databases During The Design of Prodrugs and Codrugs*, P. W. Erhardt, *Metabolism Databases and High Through-put Testing During Drug Design and Development*, P. Erhardt, Ed. IUPAC Books, Blackwell Science, Oxford, U.K., 1999.

Thus, the method of the present invention provides for the general use of a distinct metabophoric chemical arrangement that is incorporated one or more times within a parent drug compound. Specifically, variations within a defined family of an arallkyl ester moiety constitute the distinct metabophoric arrangements that are incorporated one or more times into a parent drug compound such that initially there is a minimal impact upon the original desired pharmacological activity exhibited by the parent drug. The metabophore units are subject, however, to Phase I metabolic hydrolysis by one or more of the esterases, sulfatases, phosphatases, CYPs and the like. In FIG. 3, both the ABCD fragment and the E fragment that result from the metabolic hydrolysis are inactive or significantly less active, are non-toxic and are subject to subsequent metabolic and/or elimination pathways at a rate that is appropriate for a given clinical indication. Further, manipulation of the steric and electronically driven chemical constants associated with specific molecular aspects of the metabophore allows for precise calibration and fine-tuning of the rate of the metabolic hydrolysis reactions.

While the exact numbers and preferred chemical embodiments for the metabophores are ultimately dictated via optimization within each individual case of drug and indication, there are some arrangements which generally provide for the most chemically efficient and pharmacologically compatible deployments of the inventive method. In the case of the external esters, Structure 6, the preferred embodiment often reflects incorporation of not more than two metabophores. In addition, for the preferred embodiment A is absent, B and C are at least partially derivable from structural elements already present within the parent pharmacophore, D is a carboxylic ester and E is an alkyl group. In the most preferred general embodiment only a single metabophore is utilized, C is further specified to be one or two unsubstituted carbons distant from B, and E is further specified to be a simple methyl or ethyl group. In the case of the internal esters, Structure 7, the generally preferred embodiment involves deployment of just one metabophore, where A is absent, B and C are at least partially derivable from features already present within the parent pharmacophore or C is completely absent (alkyl —$(CH_2)_n$— case where n=0), D is a carboxylic ester, and E is an integral part of the inherent pharmacophore as long as its connection to D is represented by at least one, non-sterically hindered methylene unit. An arrangement which simultaneously deploys one internal ester metabophore plus one or two external ester metabophores is also a particularly useful embodiment when extremely ultra-short durations of action are being sought for a particular indication.

Figure 4:
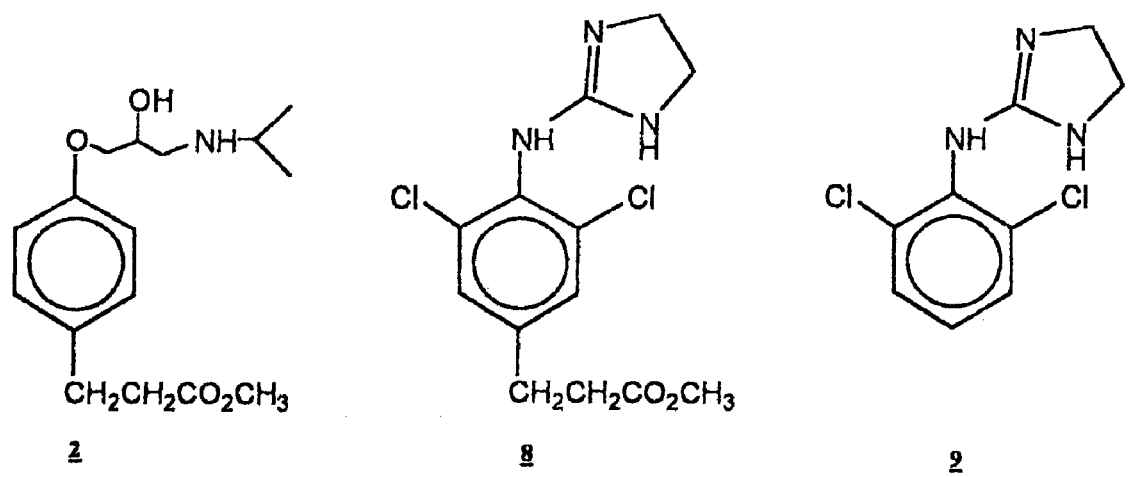
FIG. 4 shows the structural similarities between the esmolol Structure 2, a new target molecule Structure 8, and Structure 9 which is clonidine, a prototypical $\alpha_2$-adrenergic receptor agonist whose beneficial clinical effects are mediated centrally. A complementary overlap involving the key elements of the partially appended (external) metabophore within Structure 2 and a significant portion of the requisite pharmacophore within Structure 9 can be found to co-reside within the phenyl-ring of Structure 8.
Figure 6:
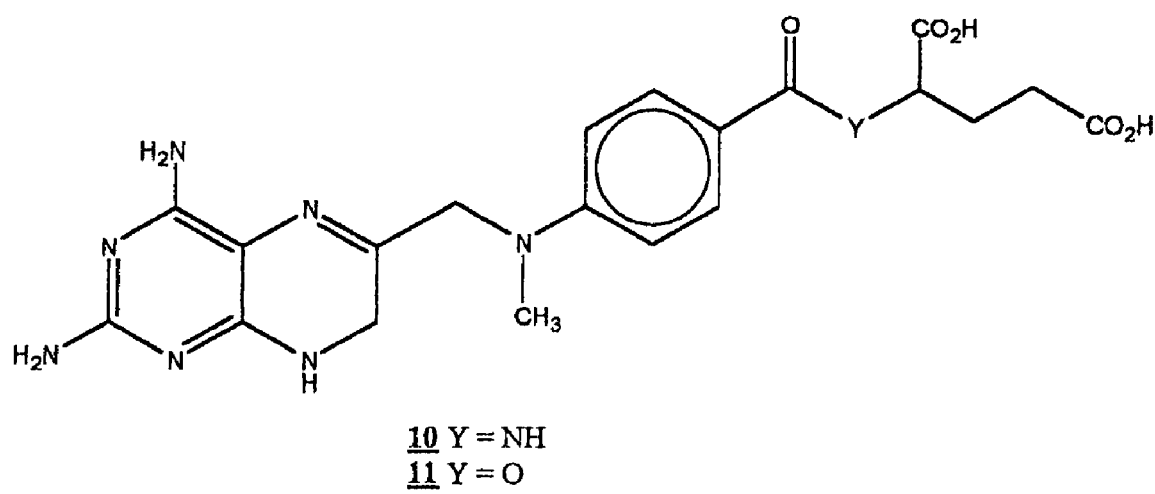
FIG. 6 shows structures of methotrexate (Structure 10) and of a metabolically labile internal ester target form (Structure 11), in which a simple ester bond is deployed as a metabophoric replacement for the parent structure's amide bond.
Figure 7:
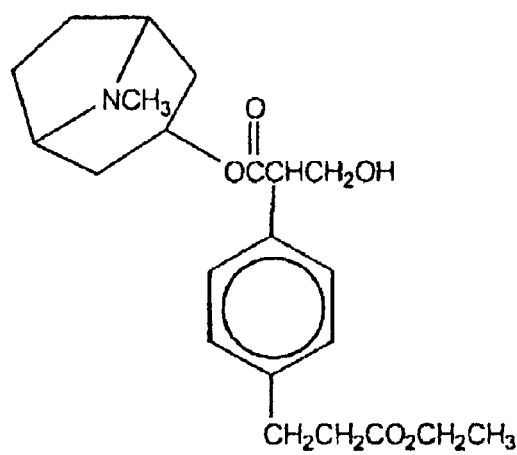
FIGS. 7–25 show further examples of the inventive method's metabophore placed within a parent molecular framework for a wide array of established pharmaceutical agents that are used clinically.
Figure 8:
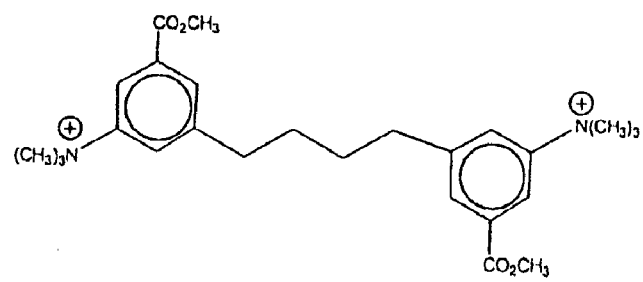
Figure 9:
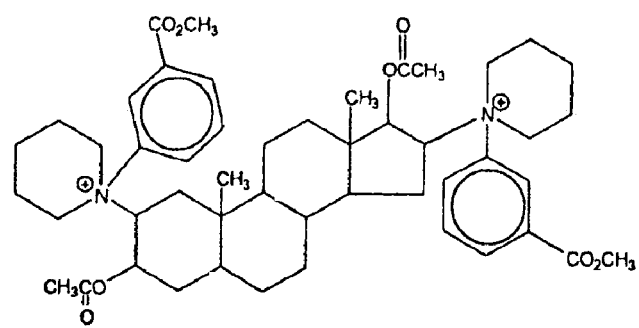
Figure 10:
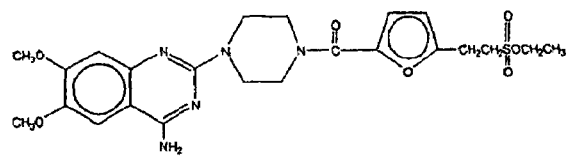
Figure 11:
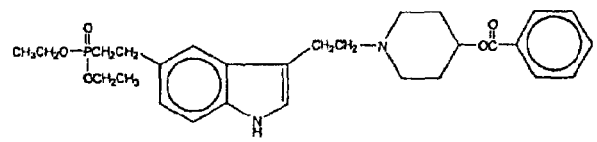
Figure 12:
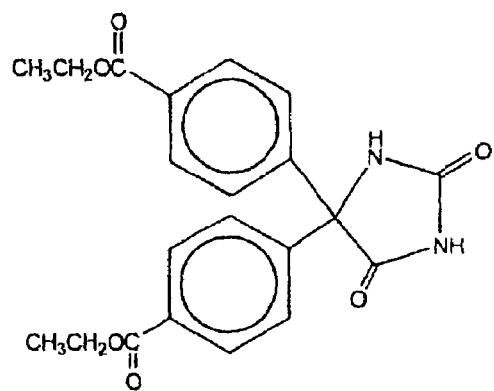
Figure 13:
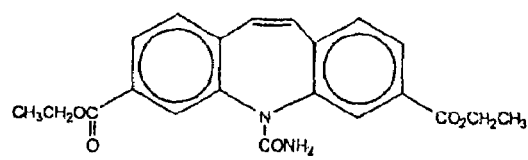
Figure 14:
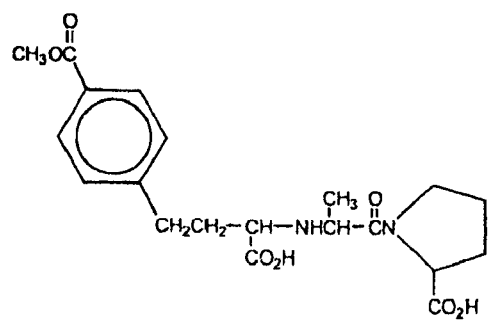
Figure 15:
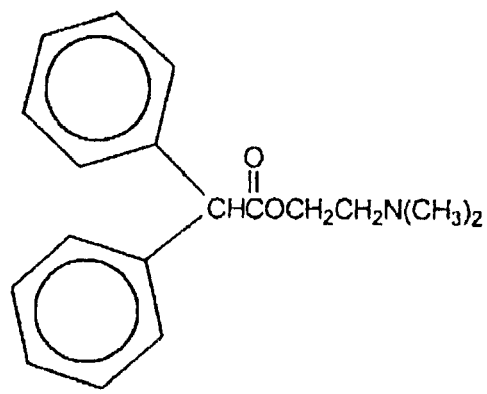
Figure 16:
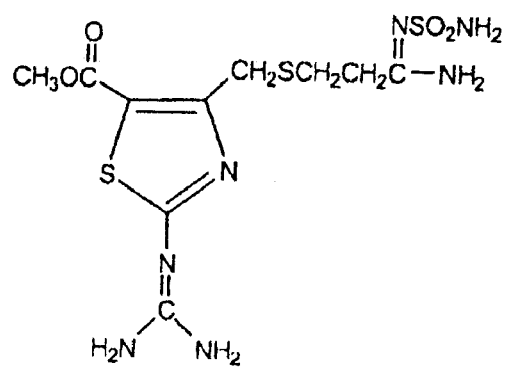
Figure 17:
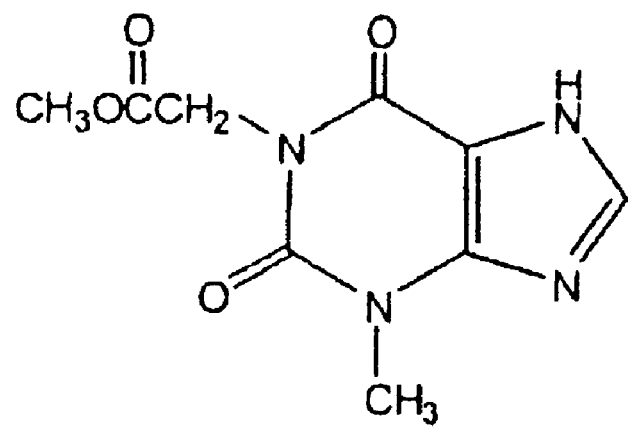
Figure 18:
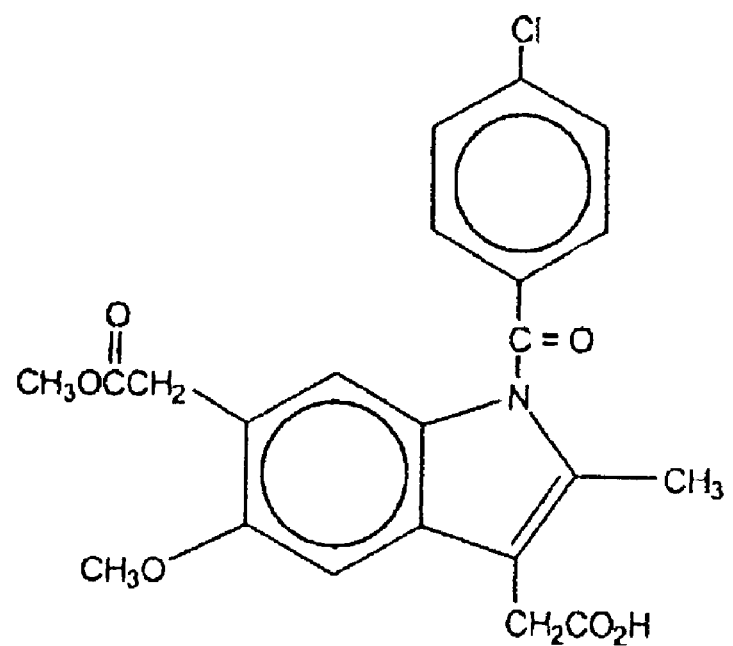
Figure 19:
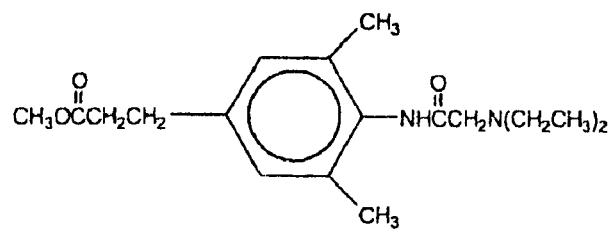
Figure 20:
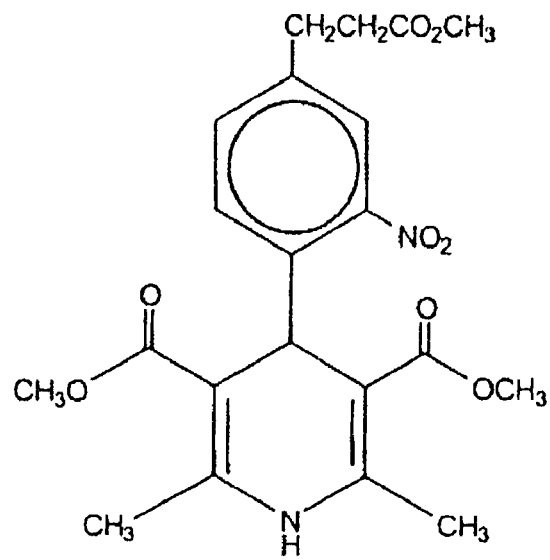
Figure 21:
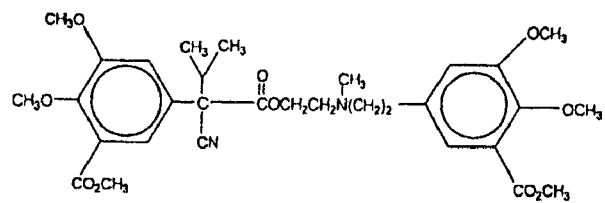
Figure 22:
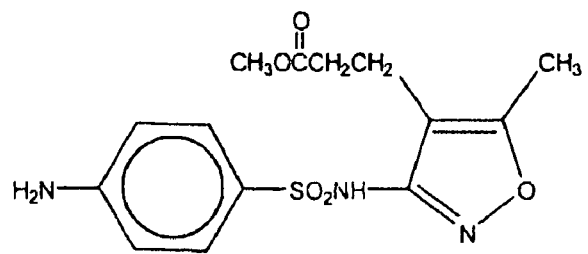
Figure 23:
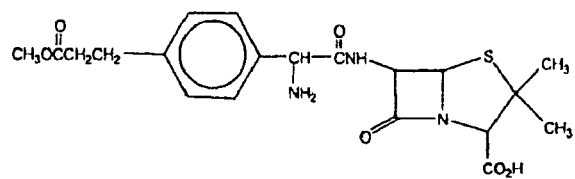
Figure 24:
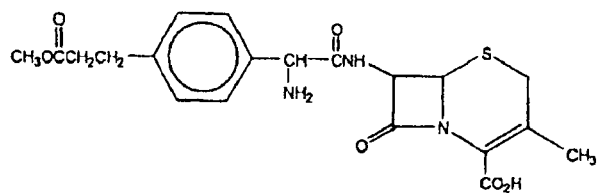
Figure 25:
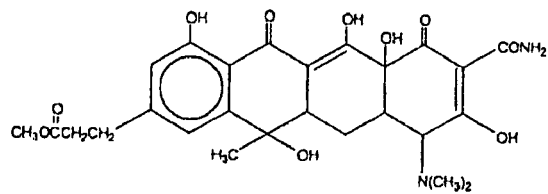

Referring now to FIGS. 4 and 6, target Structures 8 and 11 depict preferred embodiments for the respective external and internal metabophores of the inventive method as applied to two completely different types of parent molecules. To expedite drug design and development, these target structures are given the highest priority for chemical synthesis and pharmacological evaluation. Subsequent family members are constructed according to the specifications of Structures 6 and 7 on as needed basis in order to further progress and fine-tune the nature of the metabophoric insertions and to thereby best accommodate a given clinical indication. From these figures it can be noted that the present invention provides a ready blueprint for how to expeditiously address DME properties as new lead compounds proceed through the process of drug discovery and development by deploying a hierarchy of actual, practically selected, chemical structures accompanied by experimentally derived pharmacological test results. In this context the inventive method, as disclosed herein, clearly distinguishes itself from the present trend to use theoretical or computational methods accompanied by various searching paradigms across real or virtual compound libraries in order to select compounds that are then synthesized and subjected to experimental pharmacological verification, all being done in a reiterative fashion so as to finally proceed toward an applicable metabophoric lead arrangement that might then be likewise deployed via actual structures in a given, ongoing case of new drug development: e.g. *Quantitative Structure-Metabolism Relationships: Steric and Nonsteric Effects in the Enzymatic Hydrolysis of Noncongener Carboxylic Esters*, P. Buchwald and N. Bodor, *J. Med. Chem.*, 42, 5160 (1999).

The inventive technology is further illustrated in FIGS. 7–25 which show specific target structures and in the following examples which are meant to demonstrate the wide, general applicability of the invention while also providing a purview of how the metabophores can be specifically incorporated across a wide variety of structural types within the framework of actual chemical compounds. These representative examples are not intended to necessarily depict the most preferred embodiments of the invention, nor are the examples meant to be limiting in the sense of the general scope of the overall method.

EXAMPLE 1

Structure 12 represents an analog of atrorine that has an appended external ester metabophore. It has been designed for delivery as drops to the eye where it will then display its characteristic antimuscarinic properties that are useful during eye examinations for only about 30 minutes. Atropine's several hour duration is in large excess of the time typically needed to conduct a routine eye exam and chemical antidotes often need to be administered so that a patient's vision can be more quickly normalized. In addition, due to the same metabolic programming, the soft drug analog has a better systemic side-effect profile than atropine because the soft drug that is absorbed from this localized topical compartment is readily deactivated.

EXAMPLE 2

Structures 13 and 14 represent metabophore-containing, bulky analogs of decamethonium and pancuronium, respectively. Two external esters have been deployed in each case in order to further enhance the overall molecules' metabolic biotransformations given that these esters' close placements to the bulky aromatic rings slow their individual metabolic hydrolyses rates. The parent compounds' inherent antinicotinic activities, produced in a non-depolarizing fashion at neuromuscular junctions by virtue of the presence of the bulky functionalities, has a short half-life due to the appended metabophores. These compounds are ideally suited for use during surgery where there is a long-standing need for titrable, short-acting, non-depolarizing neuromuscular junction blocking agents: *Approaches to Short-Acting Neuromuscular Blocking Agents: Nonsymmetrical Bistetrahydroisoquinolinium Mono-and Diesters*, N. C. Dhar, R. B. Maehr, L. A. Masterson, J. M. Midgley, J. B. Stenlake and W. B. Wastila, *J. Med. Chem.*, 39, 556 (1996).

EXAMPLE 3

Structures 15 and 16 represent metabophore-containing analogs of prazosin and indoramin, respectively. Structure 15 contains a single sulfonate ester appendage while Structure 16 contains both an internal carboxylate metabophore and an external phosphonate ester appendage. In both cases, the inherent $\alpha_1$-receptor antagonist properties are displayed as an ultra-short duration such that both compounds are better used in critical care settings via the intravenous route to treat hypertensive crises, shock or Raynaud's disease,

EXAMPLE 4

Emergency room medical practice requires a titrable, quickly equilibrating and short action version of clonidine, Structure 9 in FIG. 4. This drug is also an a-adrenergic receptor ligand. Consideration of the structure-activity relationships for this family of centrally acting $a_2$-adrenergic agonists indicates that while the two ortho-chloro substituents are important for establishing a twisted conformation required at central $a_2$receptors, the para-position is amenable to structural modifications. *Principles of Medicinal Chemistry*, W. O. Foye, T. L. Lemke, D. A. Williams; Eds., Williams & Wilkins Publ., Baltimore, Md., p. 356 (1995). Incorporation of a single external ester metabophore according to the structural blueprint provided in FIG. 3 affords Structure 8 in FIG. 4. Since Structure 8 is a more lipophilic version of the parent structure, it equilibrates more quickly into the CNS when administered by the IV route. Thereafter, the modified soft drug version possesses a very short pharmacological half-life due to the metabolic liability of the added ester link coupled with the foreign look that its resulting metabolite displays to the a-adrenergic receptor, e.g. a full-blown carboxylate anion in a region otherwise present as a lipophilic aryl moiety. In addition, the titratable, short-acting analog is useful toward affecting the controlled withdrawal of these types of parent compounds which, in turn, are useful toward preventing 'rebound' hypertension. The structural similarities between the clonidine Structure 9, target molecule Structure 8 and the prototypical esmolol Structure 2 are all shown in FIG. 4 in a side-by-side fashion.

EXAMPLE 5

Structures 17 and 18 represent metabophore-containing analogs of phenytoin and carbamazepine, respectively. Both compounds contain two external ester metabophores which serve to prompt a rapid hydrolytic-based metabolic clearance of the compounds. Because of the programmed and controlled elimination, both analogs are able to negate the present high degree of variance found in the metabolism of the parent drugs, e.g. phenytoin saturates its metabolizing systems and thus its metabolism tends to slow down with time while carbamazepine induces its metabolizing enzymes and its metabolism tends to speed up with continued usage. Both of the parent compounds inhibit the sodium channel and find use in the treatment of seizures. As re-designed according to the inventive method's blueprint, these desirable properties are preserved within the soft drug analogs.

Further chemical adjustment of the esters' immediate steric environments within each of the analogs are able to program a specific duration of action and elimination which is then also paired with the rate of drug released from sustained-release or implantable dosage forms so that very even levels of the modified drug's concentrations are achieved for prolonged periods of time.

EXAMPLE 6

Structure 19 represents a metabophore-containing analog of enalaprilat. It's external aralkyl ester appendage provides a ready handle for hydrolytic metabolism and thus renders the molecule a short-acting version of the common ACE-inhibitor, providing that the resulting acidic moiety is not well tolerated when generated in this particular location. Ultimately, an effective soft drug version is conveniently deployed by the intravenous route and, having drip-rate control of its actions, used more advantageously within critical care settings.

EXAMPLE 7

Structures 20 and 21 represent metabophore-containing analogs of diphenhydramine and famotidine, respectively. In Structure 20 an internal ester has been deployed while in Structure 21 an external ester has been deployed. Because of the metabophoric placements, these analogs are short acting versions of their respective $H_1$-receptor blocker and $H_2$-receptor blocker parent compounds. The aralkyl ester soft drugs are beneficial toward use in critical care settings as quickly titrable and controllable, ultra-short-acting agents when given by intravenous infusion.

EXAMPLE 8

Structure 22 represents a titrable, quickly equilibrating and ultra-short acting version of theophylline for use in critical care settings whenever an adenosine antagonist is useful, e.g. improving airway resistance in critical neonatal and pediatric populations.

EXAMPLE 9

Structure 23 represents a titrable, quickly equilibrating and ultra-short acting version of indomethacin for use in critical care settings whenever an intra-venous anti-inflammatory agent is useful.

EXAMPLE 10

Structure 24 represents a titrable, quickly equilibrating and ultra-short acting version of lidocaine, a Class IB antiarhythmic agent. The aralkyl soft drug allows for more consistent dose-response relationships compared to the parent drug when used by the intravenous route in critical care settings.

EXAMPLE 11

Structures 25 and 26 represent titrable, quickly equilibrating and ultra-short acting versions of the calcium channel blockers nifedipine and verapamil, respectively. Structure 25 contains a single, external ester metabophore while Structure 26 contains an internal ester, as well as a pair of external ester, metabophores. Both analogs are ideally suited for use in the critical care arena, including neonatal populations.

EXAMPLE 12

Structures 27, 28, 29 and 30 represent metabophore-containing analogs of sulfamethoxazole, ampicillin, cephalexin and tetracycline, respectively. All of these antibiotics are designed to exhibit ultra-short durations of action which are useful not only in critical care settings via intravenous infusion, but are useful toward localization of their effects within the vicinity of polymeric materials used as sutures or other wound-healing implantables wherein the latter have been impregnated with any one or more of these types of antibiotic soft drugs. Toward easier elaboration of all of the methods of administration, all of the analogs are also designed so as to exhibit good aqueous solubility and stability when formulated as their acidified salts, e.g. as the hydrochloride salts of their amines.

EXAMPLE 13

Figure 5:
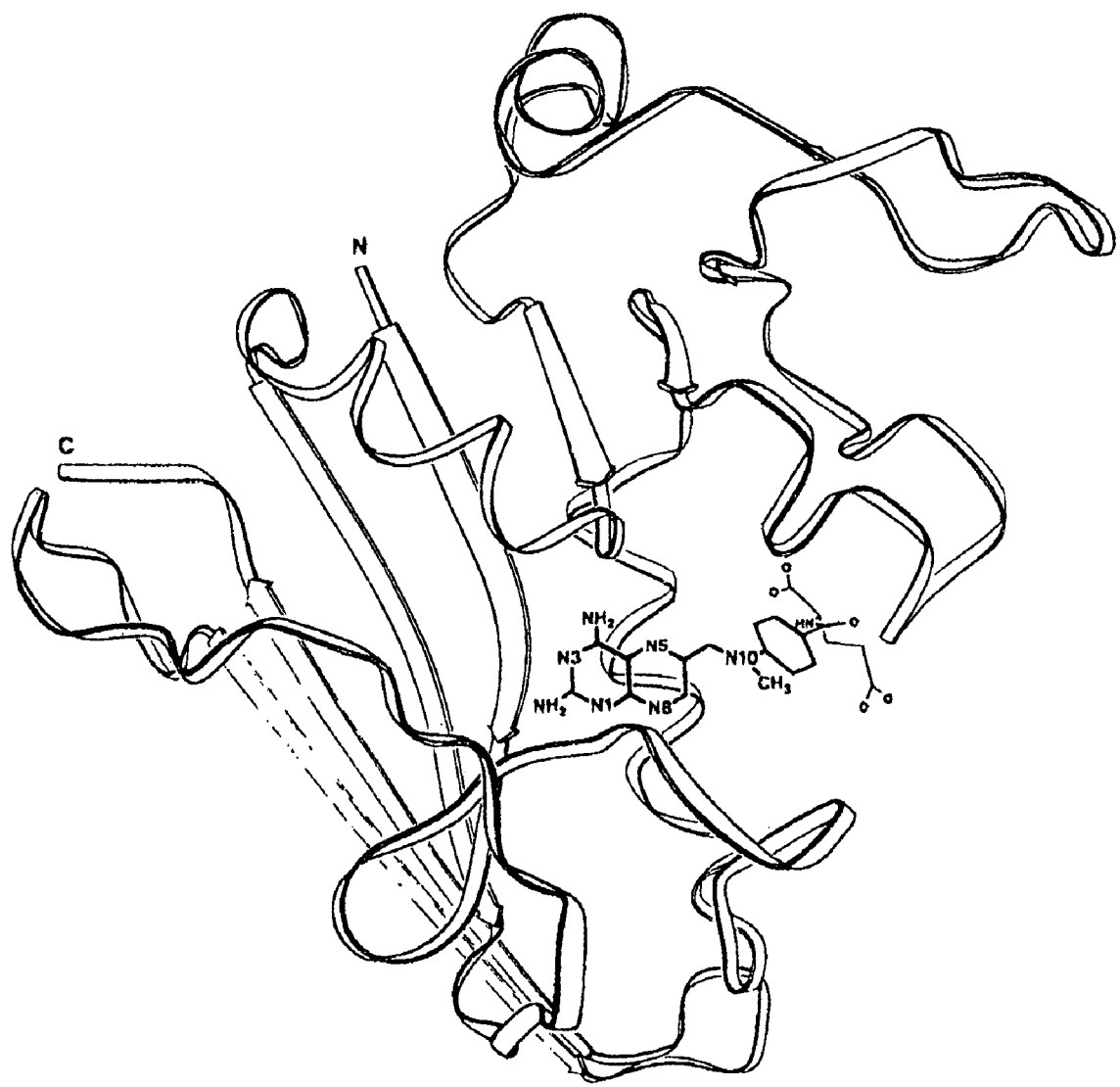
FIG. 5 shows a representation of the backbone chain folding of *E-coli* dihydrofolate reductase containing a bound methotrexate molecule as derived from a computer-generated plot of all atoms in the drug and all α-carbon atoms of the enzyme. Strands of the central pleated sheet are shown as wide arrows.

The use of methotrexate (Structure 10 in FIG. 6) for treating both epidermoid cancers and severe psoriasis is an ideal situation in which to deploy the metabophore method of the present invention so as to eliminate systemic toxicity upon percutaneous absorption after topical treatments: *The Physicians Desk Reference* (PDR) 50$^{th}$ ed., Publ: Med. Econ. Co., Montvale, N.J., p. 1276 (1996). Well-established structure-activity relationships reveal that there are three structural components which are required for the interaction of methotrexate with its biological receptor, the latter being the enzyme dihydrofolate reductase (DHFR). Therefore, placement of a labile ester metabophore between any two of these elements (e.g. internal ester) results in inactive metabolites upon hydrolysis of the metabophore. This situation is shown in FIG. 5 where the Structure 10 is depicted in its interaction with DHFR: D. A. Matthews, et al., *Science*, 297, 452 (1977). The importance of the two glutamate carboxyl groups relative to the rest of the molecule is clear, as is the rather non-demanding region immediately surrounding the glutamate-p-aminobenzoic acid amide bond. Thus, replacement of this amide bond with that of an ester is tolerable for activity, yet allows for placement of a preferred internal-ester type metabophore unit that when hydrolyzed, inactivates the parent molecule. A side-by-side structural comparison between methotrexate, Structure 10, and its internal ester metabophore version, soft drug Structure 11, is provided in FIG. 6.

EXAMPLE 14

FIGS. 7–25 show further examples of the inventive method's metabophore placed within a parent molecular framework for a wide array of established pharmaceutical agents that are used clinically.

One skilled in the art will readily appreciate that the present invention is well adapted to carry out the objects and obtain the ends and advantages mentioned, as well as those inherent therein. The present example along with the methods, procedures, treatment, molecules and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims. Any patents or publications mentioned in this specification are indicative of the levels of those skilled in the art to which the invention pertains. These patents and publications are herein incorporated by reference to the same extent as if each individual publication was specifically and individually indicated to be incorporated by reference.

Having described presently preferred embodiments of the invention, it is to be understood that there may be other embodiments which are within the scope of the appended claims.

I claim:

1. A method for modifying phenytoin, having the formula

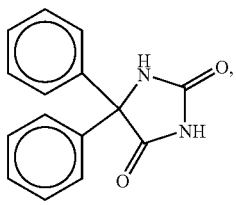

by forming a predetermined chemical arrangement within phenytoin, whereby the modified phenytoin has the formula

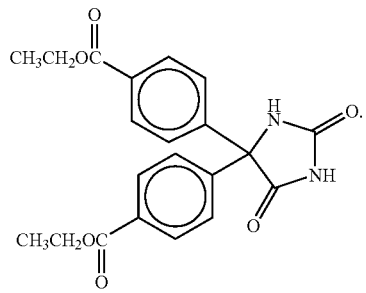

2. A method making a phenytoin-modified compound consisting essentially of the steps:

a) attaching one predetermined ester arrangement to the para-position on one of phenytoin's two aromatic rings and a second predetermined ester arrangement to the para-position on the other of phenytoin's two aromatic rings;

b) producing esterase-related metabolites for the attached arrangements using chemical hydrolysis of the esters, whereby the modified phenytoin has the formula

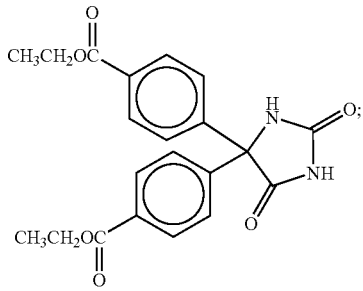

and, c) determining: i) the efficacy for the intact ester arrangement in the phenytoin-modified compound; ii) the reduced efficacy for the related metabolite; and, iii) the half-life duration for conversion of the phenytoin-modified compound to the related metabolite within human blood.

* * * * *